United States Patent [19]

Fabunan

[11] Patent Number: 5,492,901
[45] Date of Patent: Feb. 20, 1996

[54] COBRANIN-F INJECTION ENVENOMATION ANTIDOTE

[76] Inventor: Ruben G. Fabunan, 329 N. Vendome St., Los Angeles, Calif. 90026

[21] Appl. No.: 292,326

[22] Filed: Aug. 16, 1994

[51] Int. Cl.$^6$ .................................................. A01N 45/00
[52] U.S. Cl. ........................................ 514/171; 514/829
[58] Field of Search ...................... 514/829, 171

[56] References Cited

U.S. PATENT DOCUMENTS

| | | | |
|---|---|---|---|
| 2,382,546 | 8/1945 | Curtis | 424/101 |
| 3,504,083 | 3/1970 | Philpot, Jr. | 424/101 |
| 4,012,502 | 3/1977 | Philpot, Jr. | 424/98 |
| 5,053,492 | 10/1991 | Rael et al. | 530/387 |
| 5,089,415 | 2/1992 | La Dura | 435/269 |

OTHER PUBLICATIONS

Chemical Abstracts (CA) 105:20187 1986.
CA 88:293469 1987.
CA 89:36586 1978.
CA 97:53142 1982.

*Primary Examiner*—Paul J. Killos

[57] ABSTRACT

An envenomation antidote, and the process for its administration, useful for the treatment of the effects of envenomation resulting from venomous animal bites is disclosed. The antidote consists essentially of a local anesthetic and a glucocorticoid. The antidote is administered in a single dose parenterally through two routes: by subcutaneous infiltration and intramuscular injection, and by direct slow intravenous injection.

7 Claims, No Drawings

COBRANIN-F INJECTION ENVENOMATION ANTIDOTE

BACKGROUND OF THE INVENTION

1. Field of the Invention

The present invention relates to a therapeutic composition for the treatment of envenomation incidental to the bites of venomous animals, including snakes, catfish stings and other venomous animals and the process of administration thereof and, more particularly, to therapeutic compositions consisting essentially of a substantially water-soluble, injectable local anesthetic and a water-soluble glucocorticoid injectable, and to the process for administering said composition to the envenomation victim.

2. Description of the Prior Art

Traditional treatment of a venomous snakebite through the use of a serum generated from venom extracted from the particular snake in question is well known as is demonstrated in U.S. Pat. No. 4,012,502 issued on Mar. 15, 1977 to Van B. Philpot, Jr. Philpot's snake venom inhibitor is generated from a material extracted from a snake and subsequently a protein molecule is split and fragments thereof are removed along with unwanted antigenic protein material to thus separate a purified material having high inhibitor activity against snake venom toxicity and proteases. Philpot further discloses a method of purification. However, this is designed as a serum derived from the molecular modification of venom and not an antidote prepared from U.S.P. derived drugs with specific method of administration.

U.S. Pat. No. 3,504,083 issued on Mar. 31, 1970 to Van B. Philpot, Jr. discloses a method of removing the precipitate and thus detoxifying snake serum without destroying the antiplasmin action and properties of snake serum. This antiplasmin action is reported to be useful in human and animal medical procedures to prevent lysis of blood clots. However, this is the modification of a snake serum to retain an antiplasmin agent for medical use other than the treatment of snakebites and the resulting toxins derived from a snake serum and not U.S.P. derived drugs with a specific method of administration.

U.S. Pat. No. 2,382,546 issued on Aug. 14, 1945 to David Curtis discloses numerous developments of other salts of procaine which, when dissolved, in relatively high concentration, in water or glycerine, or glycol, or the derivatives of glycol will serve as media for the dissolution therein of substances which are otherwise insoluble or sparingly soluble in water, glycerine or glycol or the derivatives of glycol. However, this is the development of other salts of procaine and not the use of commonly known procaine as the mechanism of action in the treatment of snakebites and the resulting toxins as a part of U.S.P. derived drugs with a specific method of administration.

U.S. Pat. No. 5,089,415 issued on Feb. 18, 1992 to Frank M. La Duca discloses an improved method of clotting heparized blood utilizing a reagent preparation containing snake venom. This, however, does not disclose a method of treating the victim of a venomous snakebite.

U.S. Pat. No. 5,053,492 issued on Oct. 1, 1991 to Eppie D. Rael et al. discloses a method of utilizing Mojave toxin, a known snake venom toxin, to formulate tumor-specific immunotoxins, capable of attacking tumor cells and destroying tumor cell tissue.

None of the above inventions and patents, taken either singly or in combination, is seen to describe the instant invention as claimed.

SUMMARY OF THE INVENTION

Based on the survey conducted by the World Health Organization, (1954), out of the approximately 500,000 persons who are bitten each year by venomous animals, including snakes, catfish stings and other venomous animals 30,000 to 40,000 die. Other than death, the local effects of envenomation include fang punctures, swelling, discoloration of the skin and pain; whereas, the systemic characteristics include weakness, faintness, nausea, sweating and numbness. Recovery from envenomation is usually prolonged, requiring constant monitoring of the victim's body metabolism due to allergic reactions induces by prior art medications. Thus, it is apparent that an envenomation antidote which quickens recovery from the effects of envenomation would be of great benefit to both physician and patient.

There has always been a certain amount of disagreement over the proper treatment for the effects of envenomation. The most popular, although no longer recommended, prior art method of treatment consists of incision and suction at the bite site accompanied by the application of a tourniquet above the bite site. This method is no longer recommended because its use often results in infection necessitating anti-tetanus and antibiotic treatment.

The current, almost universal, method for treating the effects of envenomation consists of the administration of either monovalent antivenin or polyvalent crotaline antivenin (hereinafter referred to collectively as "PCA"). PCA is a refined and concentrated hyperimmune equine serum preparation of serum globulins obtained by fractionating blood from healthy horses immunized with the basic antigens in the venoms of all or specific members of the family Crotalidae.

PCA, however, has several disadvantages. Since PCA is an equine-serum based composition, the possibility of serum sickness, pain, muscular weakness, atrophy and anaphylaxis exists throughout the period of its administration. These PCA induced allergic reactions can be severe, and in some cases, the allergic reactions are so severe that the administration of PCA can be fatal. Corticosteroids may sometimes be used to control delayed manifestations of equine-serum allergies resulting from administration of PCA; however, corticosteroids are often ineffective. Thus the physician must balance the risk of death resulting from PCA administration with the risk of death resulting from envenomation.

Further, since PCA is not particularly potent, an enormous multiple dosage volume of PCA must be administered to the victim. Generally, from 20 milliliters to 200 milliliters is administered in multiple doses, with the normal total dosage being 100 milliliters to 150 milliliters. However, it is not uncommon in cases of extreme envenomation for a total of 300 milliliters of PCA to be administered. The World Health Organization has noted that although PCA remains the single most important factor in the treatment of envenomation, it has not reached its recommended potency. Thus, because of widespread sensitivity to PCA, the enormous volume of PCA that must be administered is a significant disadvantage.

PCA is also disadvantageous since injections into fingers, toes or other small extremities are not recommended. These body areas contain terminal arteries, and thus there is not an adequate circulation system for the PCA. In such cases, part of the initial dose of PCA must be injected intramuscularly or subcutaneously at various sites around the limb and above the level of swelling. Unfortunately, this results in not having immediate treatment of the affected area, thereby slowing if not eliminating the therapeutic value of PCA.

The administration of PCA also has several disadvantages. Since the possibility of allergic reactions including anaphylaxis exists, several precautionary tests must be performed prior to and during its use. Blood must be drawn for baseline laboratory studies. These blood studies must be done at daily intervals, depending on the severity of envenomation and on the victims response to PCA. Urine samples must be obtained at frequent intervals for microscopic examination. Skin sensitivity tests must be performed prior to administration of PCA. This is especially important for victims who have a history of allergy or sensitivity to equine-serum. If the skin test is positive, administration of PCA itself can be as fatal as envenomation.

The administration of PCA also has several practical disadvantages. A fairly sophisticated hospital is required due to the required blood, urine and skin testing, and constant monitoring of the victim. Further, PCA is fairly expensive and not readily accessible in developing and underdeveloped countries such as Burma, Africa, India, The Mideast, Latin America, and other Asian countries where the incidence of envenomation is high.

Accordingly, it is a general object of the present invention to provide an envenomation antidote which is potent, which does not induce serious allergic reactions and which can be simply administered in a single, low volume dose.

Another object of the present invention is to provide an envenomation antidote which does not require extensive blood, urine or skin tests.

It is still a further object of the present invention to provide an envenomation antidote which is capable of being inexpensively produced for immediate use and is readily available in local hospitals of underdeveloped and developing countries.

These and other objects of the present invention will become readily apparent upon further review of the following specifications.

BRIEF DESCRIPTION OF THE DRAWINGS

There are no figures or drawings in this case.

DETAILED DESCRIPTION OF THE PREFERRED EMBODIMENT(s)

The present invention is an envenomation antidote useful for the rapid treatment of envenomation by venomous animals including snakes, catfish stings and other venomous animals. The antidote is prepared from U.S.P. derived drugs and is administered parenterally in two simultaneous routes: by subcutaneous infiltration and intramuscular injection and by intravenous injection.

The antidote consists essentially of a water-soluble local anesthetic and a glucocorticoid. The term local anesthetic refers to procaine hydrochloride injection, U.S.P. with epinephrine (as the hydrochloride). Procaine hydrochloride is the preferred local anesthetic of the ester type as it is the least toxic of other known local anesthetics. However, since procaine hydrochloride produces vasodilation, a vasoconstrictor such as epinephrine is added to the procaine hydrochloride to reduce the vasodilating effects and consequent rapid removal of procaine hydrochloride from the site of infiltration and injection.

The operative amount of the procaine in the local anesthetic in aqueous solution ranges from about 5 to about 20 milligrams of procaine per milliliter of the local anesthetic. Preferably, the local anesthetic is the commercially-available procaine hydrochloride, injection, U.S.P. (20 mg/ml), 2% with epinephrine (as the hydrochloride) 1:50,000.

The term glucocorticoid refers to dexamethasone sodium phosphate. The operative amount of the dexamethasone sodium phosphate in the aqueous dexamethasone sodium phosphate solution ranges from about 4 to about 8 milligrams per milliliter. Preferably, the glucocorticoid is the commercially-available dexamethasone sodium phosphate, injection, U.S.P., 4 milligrams (of Dexamethasone phosphate) per milliliter.

The dosage of the antidote depends upon several factors including age, weight, sex, severity of envenomation and the response to treatment. The dose of the antidote ranges from about 5 milliliters to about 20 milliliters. Generally, a typical 39 year old, 120 pound male, having severe envenomation from snakebite is administered a total of 20 milliliters of the antidote.

The antidote is prepared by sterilely transferring the procaine hydrochloride with epinephrine solution and the dexamethasone sodium phosphate solution into a sterile syringe followed by gentle mixing. Prior to use, syringes and needles should be sterilized, preferably commercially available sterile syringes and needles should be used.

The operative amount of procaine in the antidote ranges from about 5 to about 20 milligrams per milliliter, and the operative amount of dexamethasone sodium phosphate in the antidote ranges from about 4 to about 8 milligrams per milliliter. Preferably, the volume ratio of procaine hydrochloride, injection U.S.P., 4 mg. (of dexamethasone phosphate) per ml is 9 to 1. Thus in 10 milliliters of the preferred antidote solution, as set forth in Example 1 below, there is present essentially about 180 milligrams of procaine, and about 4 milligrams of dexamethasone sodium phosphate, This solution can be stored for at least 2 years.

The following example describes the manner and process of making and using the invention and sets forth the best mode contemplated by the inventor of carrying out his invention but is not to be construed as limiting. For example, other commercially available formulations of procaine hydrochloride with epinephrine and dexamethasone sodium phosphate may be used provided the amounts of these ingredients are maintained in the operative ranges set forth above.

EXAMPLE 1

1 syringe containing 10 ml of the sterile antidote is prepared as follows:

|  | milliliters |
|---|---|
| Procaine hydrochloride, injection, U.S.P. (20 mg/ml), 2% with epinephrine (as the hydrochloride) 1:50,000 | 9 |
| Dexamethasone sodium phosphate, injection, U.S.P., 4 mg (of dexamethasone phosphate) per ml. | 1 |

The above ingredients are aseptically transferred into a sterile 10 milliliter syringe. After the ingredients are gently mixed, the antidote-containing syringe is ready for administration.

For parenteral administration, two identical antidote-containing syringes are prepared, each syringe containing an equal volume of the antidote, are prepared.

The administration of the antidote, unlike PCA, is quite simple and does not require extensive skin, blood or urine testing prior to its administration. The only testing that should be made is for allergic reaction to the procaine hydrochloride; however, such reactions are very rare.

One of the two syringes prepared as described above is used to administer the antidote parenterally by subcutaneous infiltration and intramuscular injection at, around and above the bite site in order to serve as a (blocking tourniquet). Generally, a "ring" method is commonly employed in which small urticarial wheals are formed around and above the bite site and subsequently connected by infiltration with the antidote. This first syringe is also used to administer the antidote intramuscularly at and around the areas of subcutaneous infiltration. Again, unlike PCA, use of the infiltration method allows administration of the antidote to toes, fingers and other small extremities.

Simultaneous with administration of the antidote by subcutaneous infiltration and intramuscular injection, the second syringe, prepared as described above, is used to administer the antidote parenterally by direct slow intravenous injection above the bite site or any accessible venous site. The antidote in the second syringe is injected intravenously at a rate ranging from about 1 milliliter per 10 seconds to about 1 milliliter per 15 seconds, preferably 1 milliliter per 15 seconds. Use of the well known butterfly needle method has been found most successful for the direct slow intravenous injection.

It can be seen from the above description that the present invention provides a readily available envenomation antidote which is useful for the treatment of envenomation incidental to venomous animal bites including snakes, catfish stings and other venomous animals. By combining two U.S.P. derived drugs, an envenomation antidote is formulated which can be simply administered in a single, low volume dose. Unlike the prior art method of treating envenomation, extensive blood, urine or skin tests are unnecessary. The invention provides the further advantage of allowing effective use of the antidote when the bite is located on fingers, toes and other small extremities. Furthermore, due to the inexpensive, readily available ingredients, the invention can be used in the rudimentary hospitals of underdeveloped countries envenomation is highly prevalent.

MEDICAL EXPERIMENTATION AND APPLICATION

From Sep. 19, 1975 to Sept. 21, 1975 Mr. Santiago Raguindin of Linasin, San Marcelino, Zambales, Philippines was under medical treatment in San Marcelino Emergency Hospital by Dr. Ruben G. Fabunan due to snakebite injury. In a single blind trial experiment, after an informed consent from the victim's wife, Mrs. Rosario Raguindin, the formulation aforementioned was initially administered parenterally at San Marcelino Emergency Hospital to snakebite victim, Santiago "Ago" Raguindin, 39, male, farmer, about 120 lbs. nearing his grave from the effects of the snake venom of a cobra, on Sep. 19, 1975. The injection was given with great care and confidence in a single dose. Although the popular method of first aid treatment of incision and suction at the bite site and tourniquet applied above the bite site and other snakebite measures were given by previous physicians to the victim, his condition deteriorated progressively. Commercial antivenins were not readily available at this rural hospital. Physical examination revealed unstable vital signs with blood pressure at 130/100; temperature at 36.6 degrees C., and a weak, irregular pulse. Two fang marks with oozing dark bluish blood at the dorsal aspect of the right hand with progressive edema of that extremity. Systemic manifestations of moderate to severe envenomation included blurred vision, apprehension, slurred speech, dysphagia, profuse sweating, excessive whitish sticky sputum, discoloration of the skin, acute respiratory distress and lethargy.

The aforementioned drug of the present invention was administered as previously prescribed. About 2–5 minutes after completion of the intravenous route, drug related adverse effects were noted like transient apprehension, confusion, tachycardia, sweating, complaint of thirst and fatigue with gradual response within an hour to progressive recovery. The patient remains in good health without hand deformity. Thus, the first treatment of a patient ready to expire within hours and returned to perfect health through use of the present invention and the prescribed method of administration. This is a documented account of the experimental administration and not a commercial offering of the aforementioned treatment, see attachment A.

It will be understood by those skilled in the art that the present invention is not limited to the sole embodiment described above, but encompasses any and all embodiments within the scope of the following claims.

I claim:

1. A method for the treatment of envenomation incidental to the bites of venomous animals including snakes, catfish stings and other venomous animals which comprises the injection of a sterile, liquid composition of a local anesthetic of the ester type and a glucocorticoid.

2. A method according to claim 1 wherein said sterile, liquid composition is administered in two routes: by intramuscular injection and subcutaneous infiltration at, around and above the bite site, and by slow intravenous injection above the bite site or any accessible venous site.

3. A method according to claim 2 wherein said sterile, liquid composition is directly injected intravenously at a rate ranging from about 1 milliliter per 10 seconds to about 1 milliliter per 15 seconds.

4. A sterile, liquid composition used for the treatment of envenomation incidental to the bites of venomous animals including snakes and catfish stings consisting essentially of procaine hydrochloride with epinephrine as the hydrochloride and dexamethasone sodium phosphate.

5. A sterile, liquid composition according to claim 4 wherein is present from about 5 to about 20 milligrams of procaine per milliliter, and from about 4 to 8 milligrams of dexamethasone sodium phosphate per milliliter.

6. A sterile, liquid composition according to claim 4 consisting of procaine hydrochloride, injection, U.S.P. (20 mg/ml), 2% with epinephrine (as the hydrochloride) 1:50,000 and dexamethasone sodium phosphate, injection, U.S.P., 4 milligrams (of dexamethasone phosphate) per milliliter.

7. A sterile, liquid composition according to claim 6 consisting essentially of about 9 parts by volume procaine hydrochloride, injection, U.S.P. (20 mg/ml), 2% with epinephrine (as the hydrochloride) and 1 part by volume dexamethasone sodium phosphate, injection, U.S.P., 4 milligrams (of dexamethasone phosphate) per milliliter.

* * * * *